United States Patent [19]

Muzykantov et al.

[11] Patent Number: 5,653,979
[45] Date of Patent: Aug. 5, 1997

[54] IMMUNOTARGETING OF PLASMINOGEN ACTIVATORS TO THE PULMONARY ENDOTHELIUM

[75] Inventors: Vladimir R. Muzykantov, Philadelphia; Elliot S. Barnathan, Havertown, both of Pa.

[73] Assignee: Trustees of the University of Pennsylvania, Philadelphia, Pa.

[21] Appl. No.: 413,415

[22] Filed: Mar. 30, 1995

[51] Int. Cl.$^6$ .................... A61K 35/16; A61K 35/42; A61K 38/36; A61K 39/395
[52] U.S. Cl. .................... 424/178.1; 530/387.1; 530/380; 530/830; 530/350; 530/388.26; 530/391.7; 424/156.1; 424/145.1; 424/181.1; 435/215; 435/216; 435/217; 435/195
[58] Field of Search .................... 424/178.1; 435/188, 435/215–217, 195; 530/380, 391.7, 387.1

[56] References Cited

FOREIGN PATENT DOCUMENTS 3996711  2/1987  U.S.S.R. .

OTHER PUBLICATIONS

Cavallaro et al., "A conjugate between human urokinase and saporin, a type-1 ribosome-inactivating protein, is selectively cytotoxic to urokinase receotpro-expressing cells," *J. Biol. Chem.* (1993) 268:23186–23190.

Danilov et al., "Monoclonal Antibodies to Angiotensin-converting enxyme: a powerful tool for lung and vessel studies," *J. Mol. Cell Cardiol.* (1989) 21:165–170.

Danilov et al., "Interaction of mAb to angiotensin-converting enxyme (ACE) with antigen in vitro and in vivo: antibody targeting to the lung induces ACE antigenic modulation," *International Immunology* (1994) 6(8):1153–1160.

Danilov, S.M. and Muzykantov, V.R., "Monoclonal antibody to angiotensin-converting enzyme," *Progress in Respiration Research* (1990) 26:85–93.

Danilov et al., "Immunohistochemical study of angiotenin-converting enzyme in human tissues using monoclonal antibodies," *Histochemistry* (1987) 87:487–490.

Danilov et al., "Radioimmunoimaging of lung vesses: an approach using indium–111–labeled monclonal antibody to angiotensin-converting enzyme," *J. Nucl. Med.* (1989) 30:1686–1692.

Danilov et al., "Lung is target organ for a monoclonal antibody to angiotensin-converting enzyme," *Laboratory Investigation* (1991) 64(1):118–124.

Danilov et al., "Monoclonal antibody to human lung angiotensin-converting enzyme," *Biotechnology and Applied Biochemistry* (1987) 9:319–322.

Fears, R., "Why targeting? Physiological, Pharmacological, and Economic Aspects," *Annals New York Acad. Sci.* (1992) 667:343–356.

Gennaro, Alfonso, Ed., *Remington's Pharmaceutical Sciences*, 18th Edition, Mack Publishing Co., Easton, PA, 1990.

Haber et al., "Antibody targeting as a thrombolytic strategy," *Annals New York Acad. Sci.* (1992) 667:365–381.

Hiemisch et al. "Purification of radiolabeled monoclonal antibodies to angiotensin-converting enzyme significantly improves specificity and efficacy of its trageting into the lung," *Nucl. Med. Biol.* (1993) 20(4):435–441.

Lijnen, H.R. and Collen, D., "Remaining perspectives of mutant and chimeric plasminogen activators," *Annals New York Acad Sci.* (1992) 667:357–364.

Mitchel et al., "Enhanced intracoronary thrombolysis with urokinase using a novel, local drug delivery system," *Circulation* (1995) 91 (3):785–793.

Muzykantov et al., "Immunotargeting of erythrocyte-bound streptokinase provides local lysis of a fibrin clot," *Biochim. Biophys. Acta* (1986) 884:355–363.

Muzykantov, V.R. and Danilov S.M., "Gluconse oxidase conjugated with anti-endothelial monoclonal antibodies: in vitro and in vivo studies," *Int. J. Radiat. Biol.* (1991) 60(1/2):11–1.

Muzykantov et al., "Immunotargeting of streptavindin to the pulmonary endothelium," *J. Nucl. Med.* (1994) 35:1358–1365.

Sakharov et al., "Two-step targeting of urokinase to plasma clot provides effiecient fibrinolysis," *Thrombosis Res.* (1988) 49:481–488.

*Primary Examiner*—Lila Feisee
*Assistant Examiner*—John Lucas
*Attorney, Agent, or Firm*—Law Offices of Jane Massey Licata

[57] ABSTRACT

A multimolecular complex made up of a plasminogen activator conjugated to anti-ACE Mab 9B9 capable of delivering the plasminogen activator to the pulmonary endothelium is provided. Methods of using this complex to selectively deliver the plasminogen activator to the pulmonary endothelium to enhance fibrinolysis in the lungs of an animal are also provided. In addition, a method of prolonging the time a plasminogen activator is present in the circulation of an animal by conjugating the plasminogen activator to anti-ACE Mab 9B9 is also provided.

2 Claims, 11 Drawing Sheets

IMMUNOTARGETING OF PLASMINOGEN ACTIVATORS TO THE PULMONARY ENDOTHELIUM

BACKGROUND OF THE INVENTION

Acute and chronic thrombotic states are major causes of morbidity and mortality in many industrialized countries. Occlusion of blood vessels by thrombus or fibrin clots plays an integral role in both heart and pulmonary disease. Plasmin is a protease with relative broad substrate specificity. In blood, plasmin cleaves fibrin, thus, resulting in lysis of the fibrin clot. Effective therapies must also be capable of lysing these fibrin clots.

One approach to the treatment of an established thrombosis is the pharmacological dissolution of the blood clot via intravenous infusion of plasminogen activators. Plasminogen activators are proteolytic enzymes possessing specific proteolytic activity towards the blood plasma protein plasminogen. There are several plasminogen activators (PA) including, but not limited to, tissue-type PA (t-PA), urokinase PA (u-PA: including the proenzyme form referred to as prourokinase, or single chain urokinase PA (scu-PA); high molecular weight two chain uPA and low molecular weight uPA), and streptokinase, which are capable of converting inactive zymogen plasminogen to the active enzyme, plasmin, by specific cleavage of plasminogen. Plasmin digests fibrin to soluble degradation products, thus, eliminating the clot. Plasminogen activators have been demonstrated to cause marked decreases in plasminogen and fibrinogen concentrations while increasing thrombin time, activated partial thromboplastin time and prothrombin time.

All of the plasminogen activators provided are presently in worldwide clinical trials as fibrinolytic agents. Endogenous tPA and scuPA demonstrate selectivity toward fibrin, thus, few systemic effects from this treatment have been predicted. However, provision of these activators in pharmacological amounts has been found to overwhelm normal control mechanisms such as plasminogen activator inhibitors. The major problems associated with the efficacy of these agents are extremely fast blood clearance, rapid re-occlusion and hemorrhaging in tissues such as the brain. Accordingly, new therapies and delivery systems are being investigated.

The objective for the ideal fibrinolytic agent has been defined as the rapid achievement of vascular patency in all patients without early re-occlusion or bleeding. Primary aims for new therapies include increasing plasma clearance half-life, decreasing inhibitor interactions, and improving fibrin affinity and localization of the action of plasminogen activator(s) in definitive sites of the vasculature. Sites of fibrin clot formation, sites of deposition or embolization of fibrin clots and sites with high probability of vascular occlusion by fibrin clots represent such definitive sites of the vasculature. Mitchel et al. Circulation (1995) 91(3):785–783.

Targeted delivery of these activators to the site of clot formation has been performed in a number of different manners. Plasminogen activators have been artificially conjugated with monoclonal antibodies to fibrin providing the plasminogen activator with an affinity for the clot. Fears, R., *Annals New York Acad. Sci.* (1992) 667:343–356; Lijnen, H. R. and Collen, D., *Annals New York Acad. Sci.* (1992) 667:357–364; and Haber et al., *Annals New York Acad. Sci.* (1992) 667:365–381. Bi-specific antibodies possessing affinity to both the plasminogen activator and to fibrin have also been constructed for selective accumulation of plasminogen activators in the fibrin clots. Sakharov et al. *Thrombosis Res.* (1988) 49:481–488. Plasminogen activators have also been conjugated to antibodies specific for collagen for selective delivery of the activator to injured sites of the vascular wall. Muzykantov et al., *Biochim. Biophys. Acta* (1986) 884:355–363. In addition, monoclonal antibodies recognizing epitopes present on the surface of activated platelets have also been suggested as a targeting vector for thrombolytic agents. Lijnen, H. R. and Collen, D., *Annals New York Acad Sci.* (1992) 667:357–364. However, the therapeutic potential of such conjugates still remains to be established.

Mutants of plasminogen activators, in particular tPA mutants, have also been constructed which possess altered pharmacokinetic properties and altered functional properties including binding and stimulation by fibrin, and resistance to plasmin and protease inhibitors. Lijnen, H. R. and Collen, D., *Annals New York Acad Sci.* (1992) 667:357–364. Mutants described to date have had markedly reduced clearances but, usually, also reduced specific thrombolytic potencies.

While several of these approaches are believed to increase thrombolytic potency and prevent rethrombosis, bleeding remains an important issue. None of these approaches provides for selective delivery of the plasminogen activator to the particular tissue where thrombus are most likely to develop, in particular the pulmonary endothelium and the heart.

A multimolecular complex has now been developed comprising a plasminogen activator conjugated to anti-ACE Mab 9B9 which is capable of delivering the plasminogen activator selectively to the pulmonary endothelium. Delivery of plasminogen activators to the surface of the pulmonary endothelium leads to increased concentrations of plasmin in the pulmonary circulation which is useful for enhancing local fibrinolysis in the lungs.

SUMMARY OF THE INVENTION

An object of the present invention is to provide a multimolecular complex comprising a plasminogen activator and anti-ACE Mab 9B9 capable of delivering the plasminogen activator to the pulmonary endothelium.

Another object of the present invention is to provide a method of selectively targeting a plasminogen activator to the pulmonary endothelium of an animal which comprises conjugating the plasminogen activator to anti-ACE Mab 9B9 to form a multimolecular complex and administering said multimolecular complex to the animal.

Another object of the present invention is to provide a method of enhancing fibrinolysis in the lungs of an animal which comprises administering to an animal an effective amount of a multimolecular complex comprising a plasminogen activator conjugated to anti-ACE Mab 9B9.

Another object of the present invention is to provide a method of prolonging the time a plasminogen activator is present in the circulation of an animal which comprises administering to an animal a plasminogen activator conjugated to anti-ACE Mab 9B9.

BRIEF DESCRIPTION OF THE FIGURES

FIG. 1 is a bargraph showing the blood levels and pulmonary uptake in rats of radiolabeled tPA, scuPA or uPA conjugated with either Mab 9B9 (filled bars) or IgG (unfilled bars) one hour after intravenous injection.

DETAILED DESCRIPTION OF THE INVENTION

It has now been found that conjugation of a plasminogen activator with the monoclonal antibody anti-ACE Mab 9B9 (hereinafter referred to as Mab 9B9) provides both specific pulmonary delivery of the plasminogen activators and prolongation of the life-time of the plasminogen activator in the circulation. By "plasminogen activator" it is meant to include any proteolytic enzyme possessing specific proteolytic activity towards the blood plasma protein plasminogen and, therefore, which is capable of converting inactive zymogen plasminogen to the active enzyme, plasmin, by specific cleavage of plasminogen. Examples of plasminogen activators (PA) include, but are not limited to, tissue-type PA (t-PA), urokinase PA (u-PA: including the proenzyme form referred to as prourokinase, or single chain urokinase PA (scu-PA); high molecular weight two chain uPA and low molecular weight uPA), and streptokinase. Selective accumulation of plasminogen activators in the lung vasculature for prolonged periods of time leads to enhanced concentrations of plasmin in the pulmonary circulation and in the heart, the first organ downstream from the lung, which is believed to be useful for effective fibrinolysis in the lung and heart.

Figure 1A:
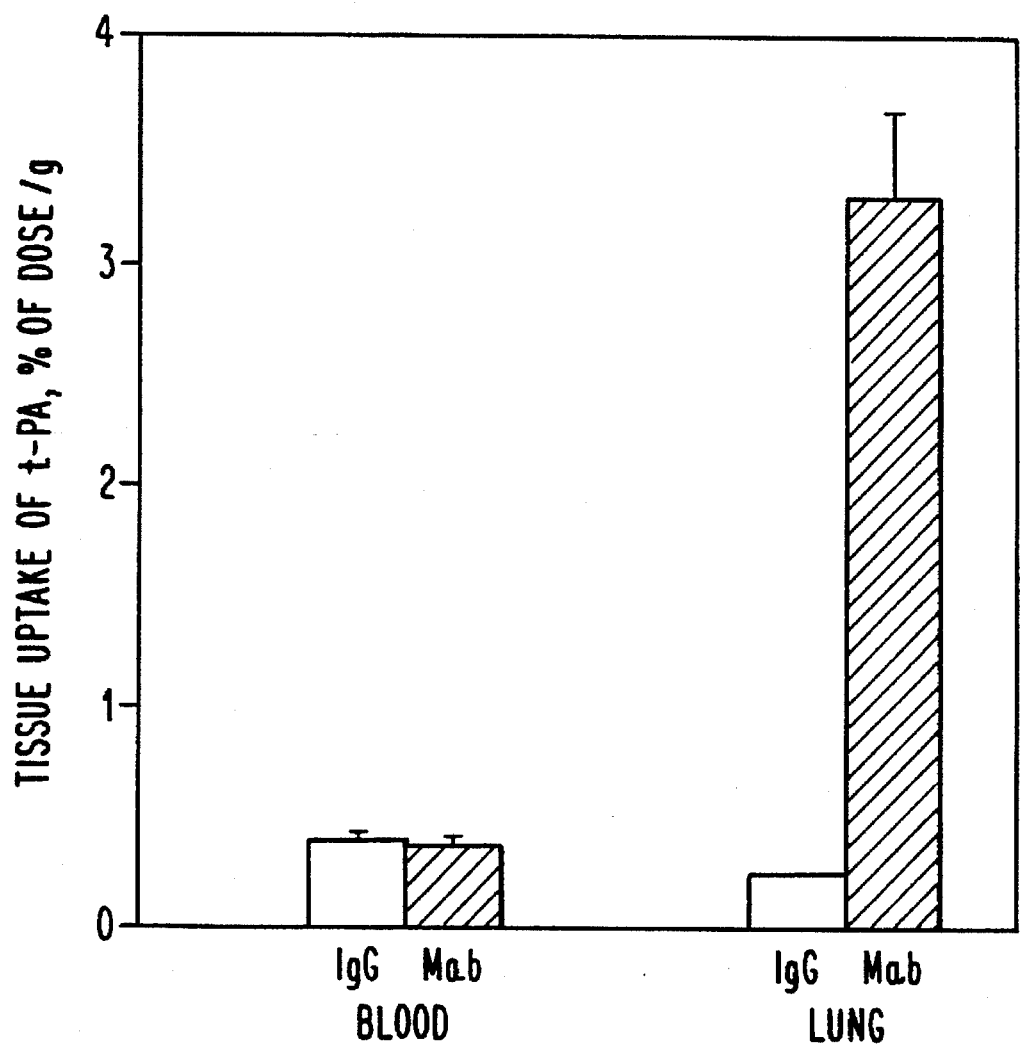
FIG. 1A shows the tissue uptake of radiolabeled tPA.
Figure 1B:
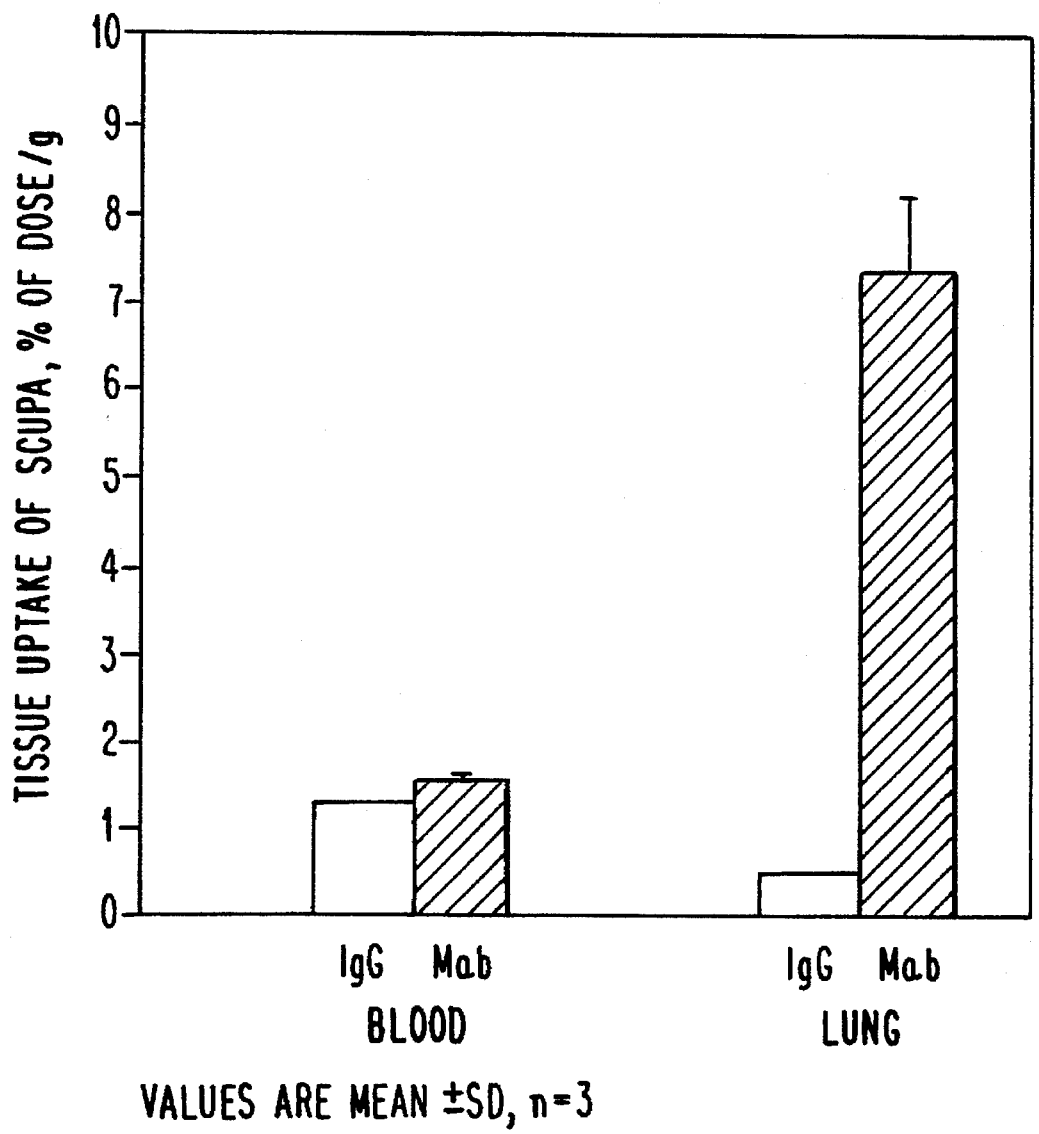
FIG. 1B shows the tissue uptake of radiolabeled scuPA.
Figure 1C:
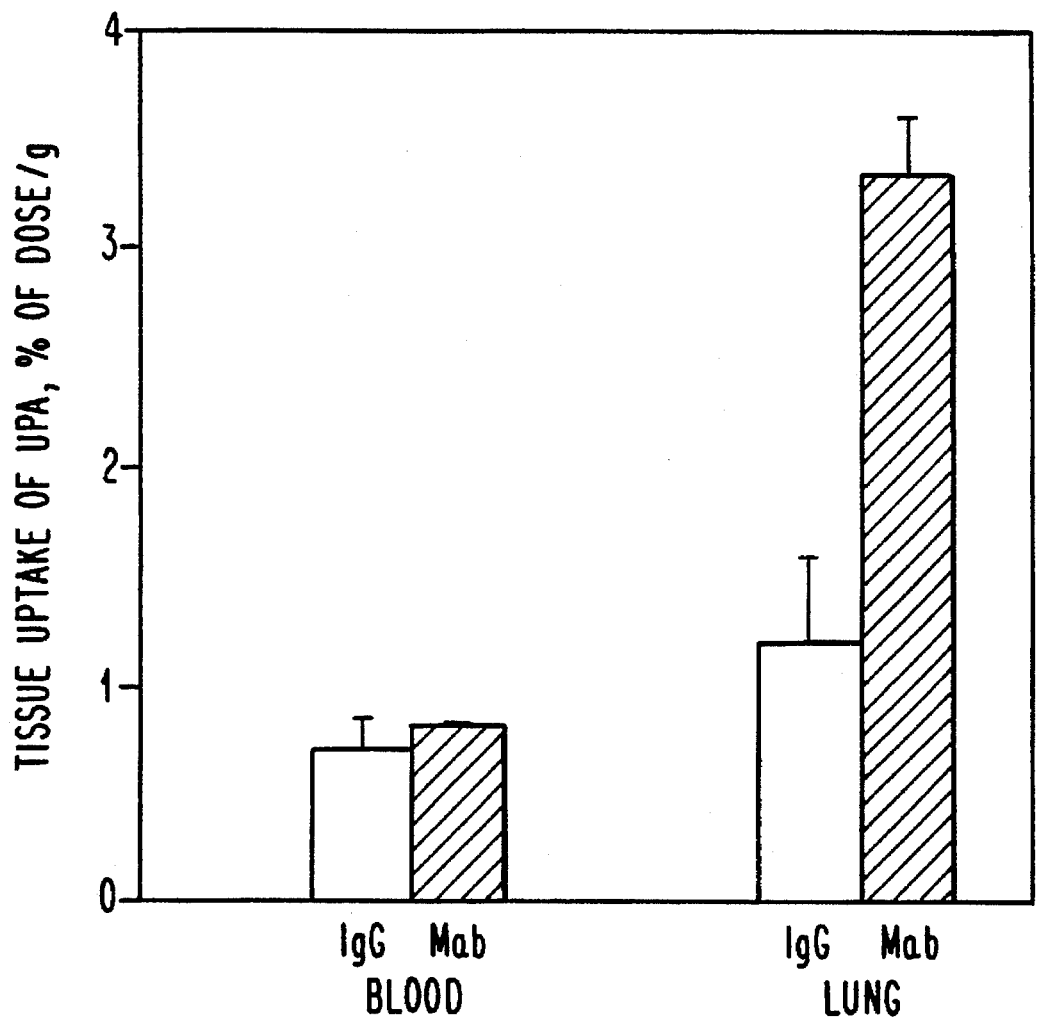
FIG. 1C shows the tissue uptake of radiolabeled uPA.
Figure 2:
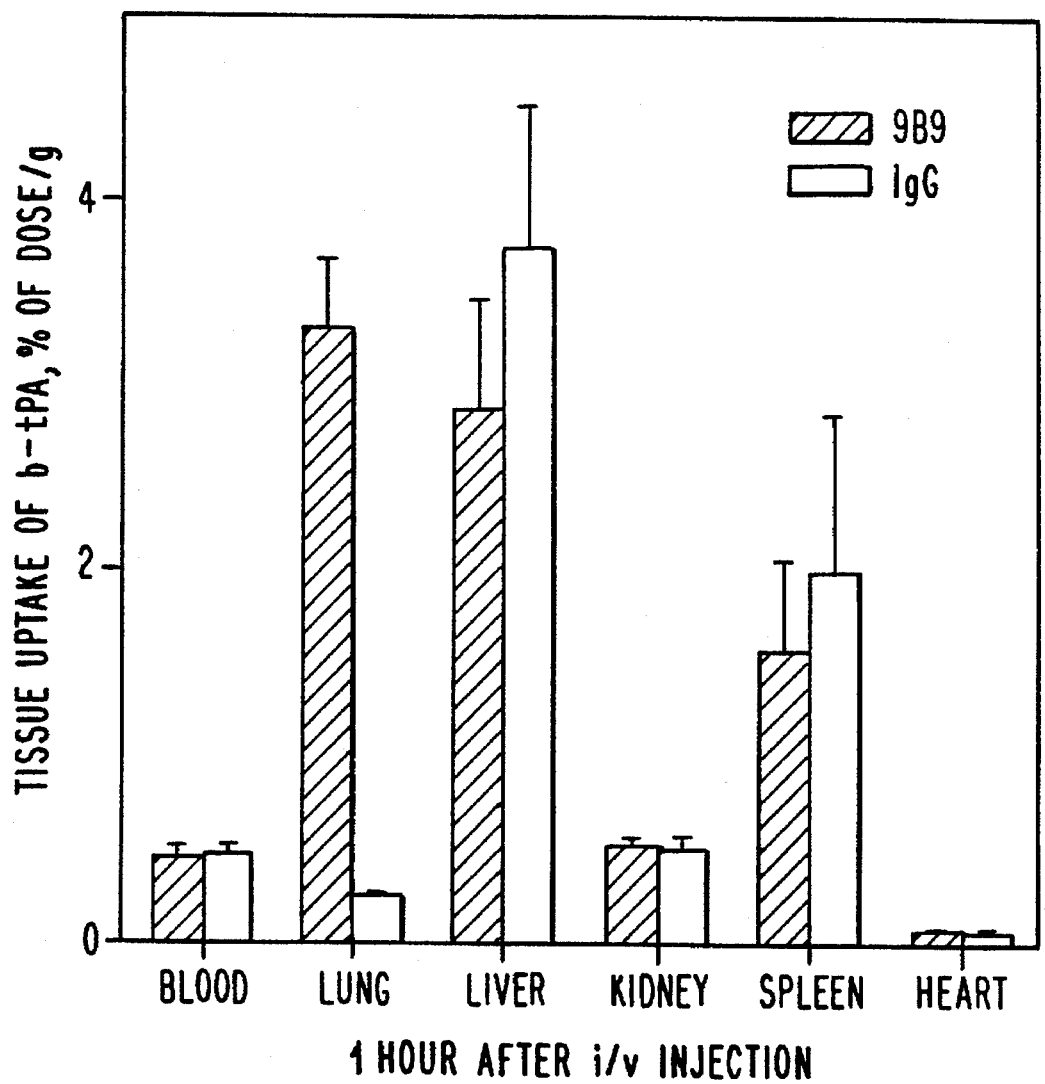
FIG. 2 is a bargraph showing the biodistribution in rats of radiolabeled tPA conjugated with either Mab 9B9 (hatched bars) or IgG (unfilled bars) one hour after intravenous injection.
Figure 3:
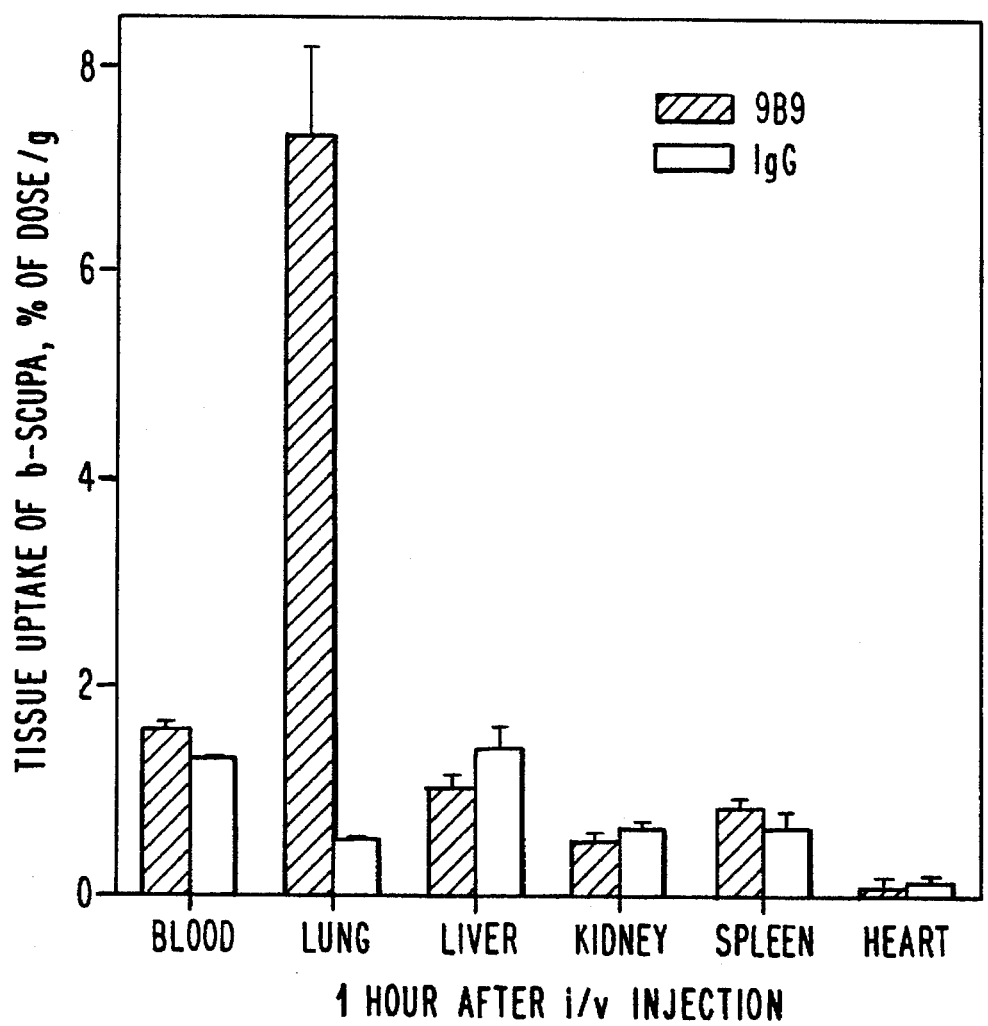
FIG. 3 is a bargraph showing the biodistribution in rats of radiolabeled scuPA conjugated with either Mab 9B9 (hatched bars) or IgG (unfilled bars) one hour after intravenous injection.
Figure 4:
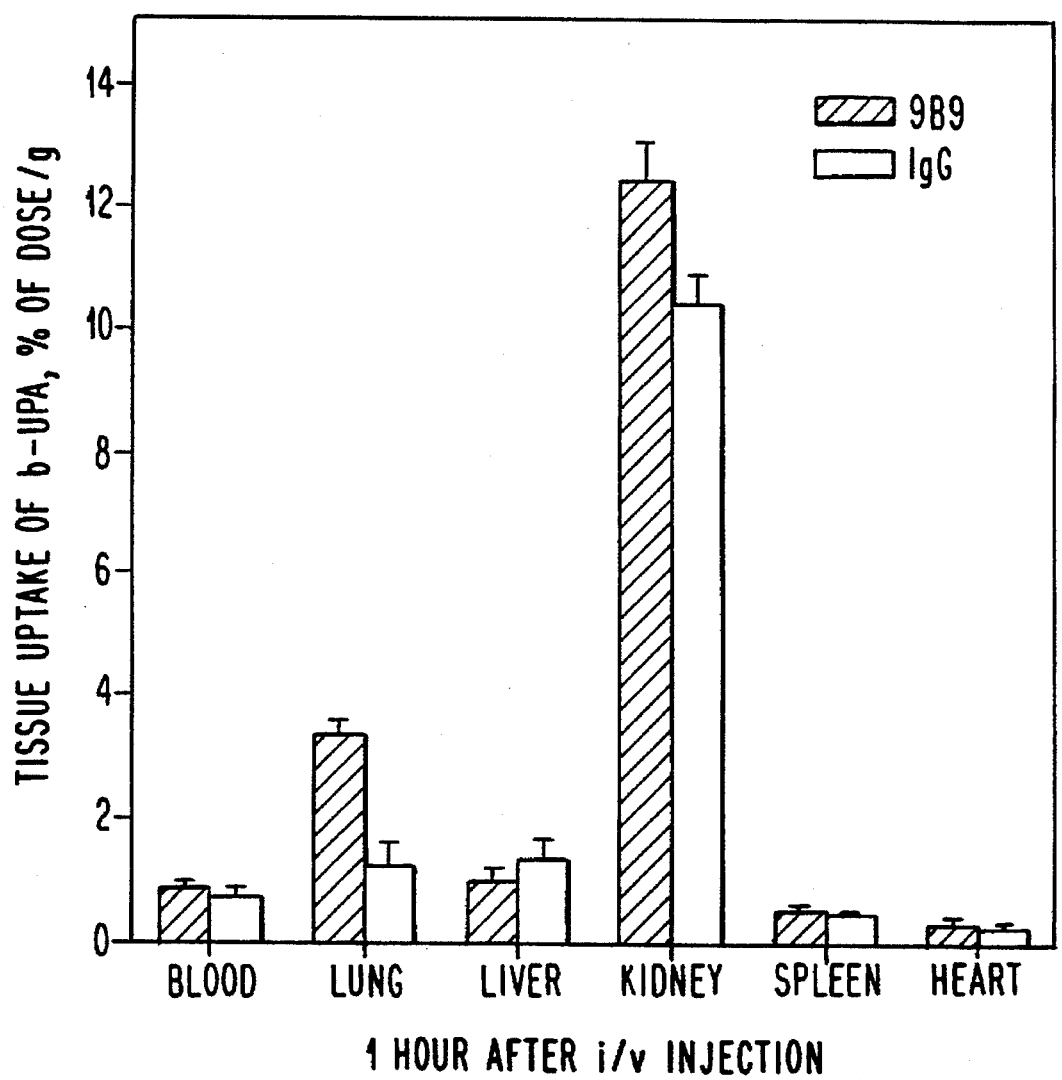
FIG. 4 is a bargraph showing the biodistribution in rats of radiolabeled uPA conjugated with either Mab 9B9 (hatched bars) or IgG (unfilled bars) one hour after intravenous injection.
Figure 5:
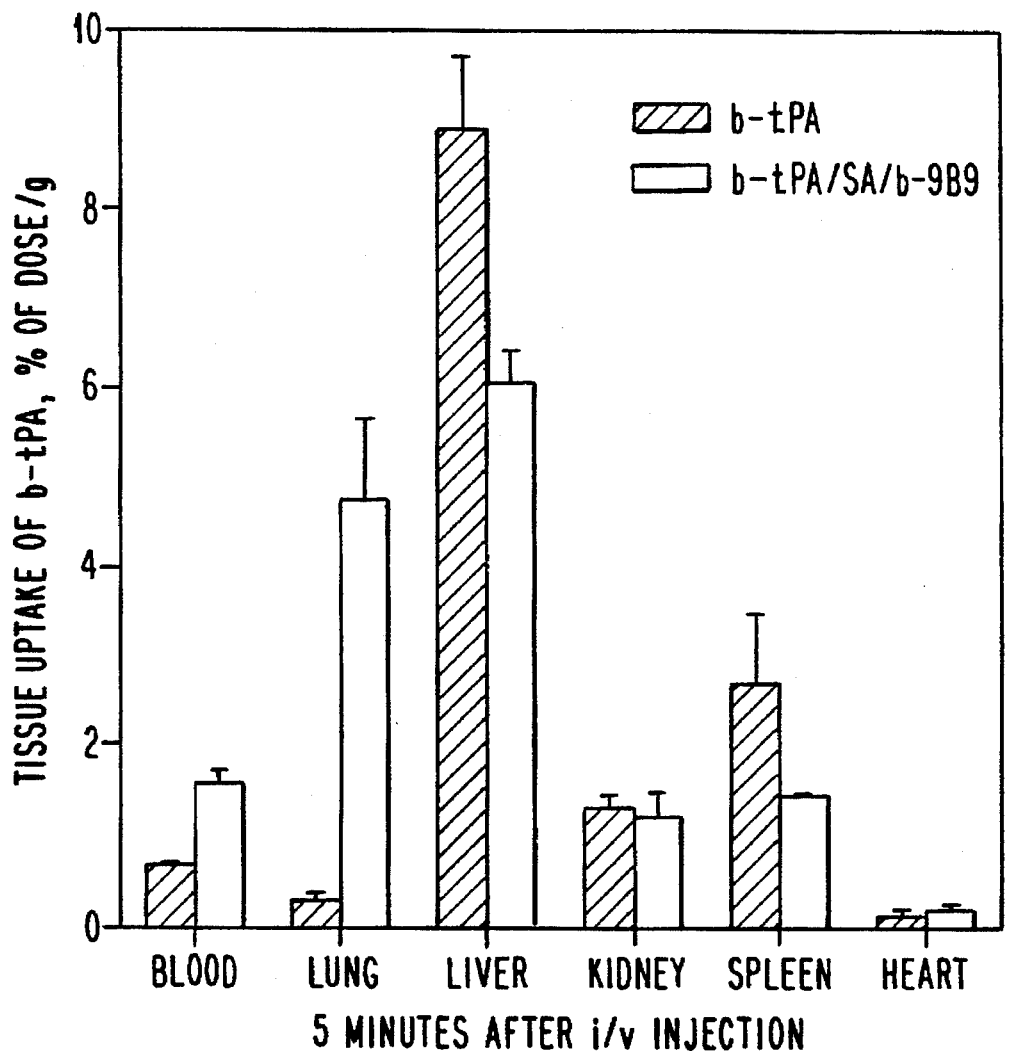
FIG. 5 is a bargraph showing the biodistribution in rats of radiolabeled tPA (hatched bars) and radiolabeled tPA conjugated with Mab 9B9 (unfilled bars) five minutes after intravenous injection.
Figure 6:
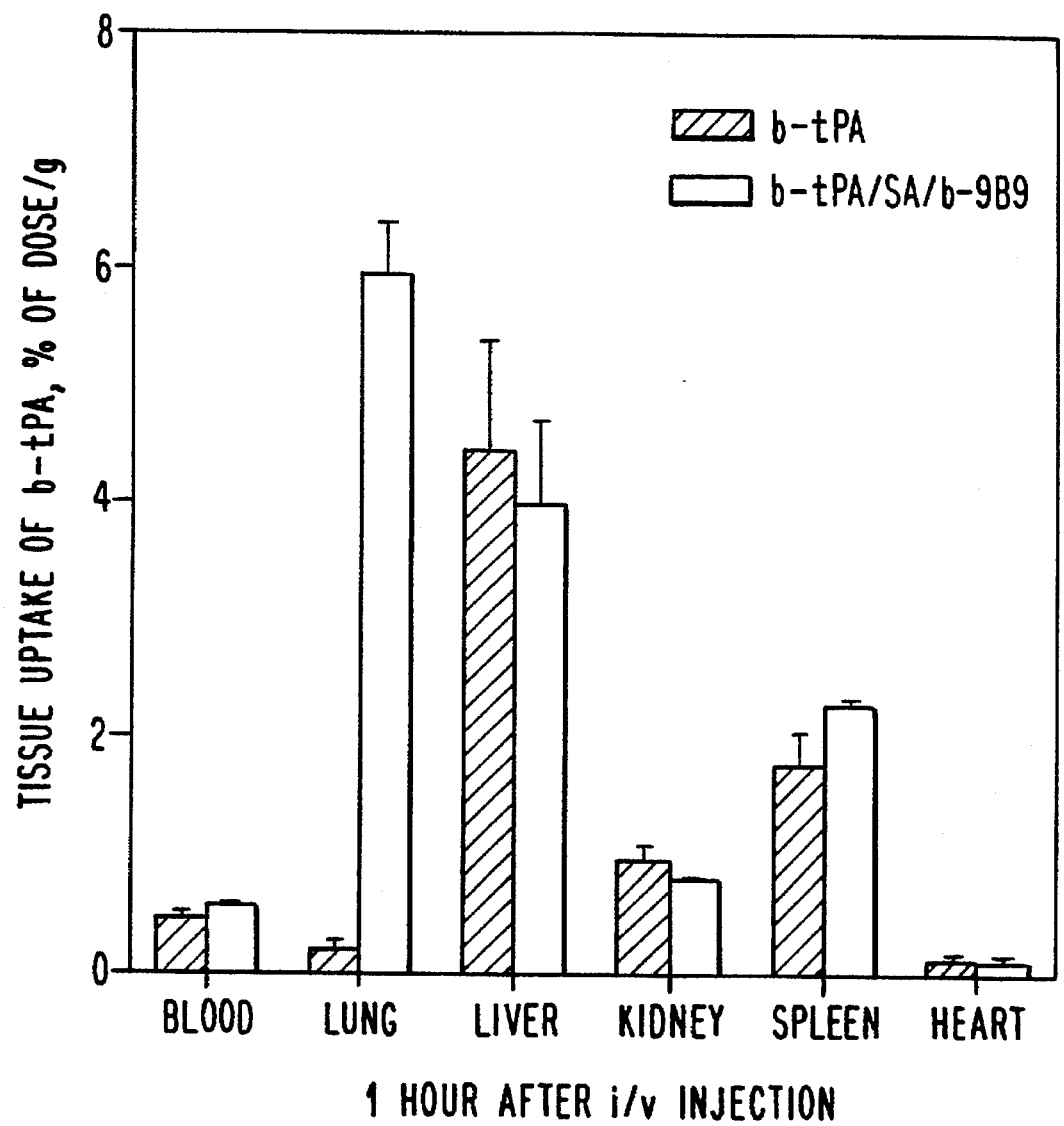
FIG. 6 is a bargraph showing the biodistribution in rats of radiolabeled tPA (hatched bars) and radiolabeled tPA conjugated with Mab 9B9 (unfilled bars) one hour after intravenous injection.
Figure 7:
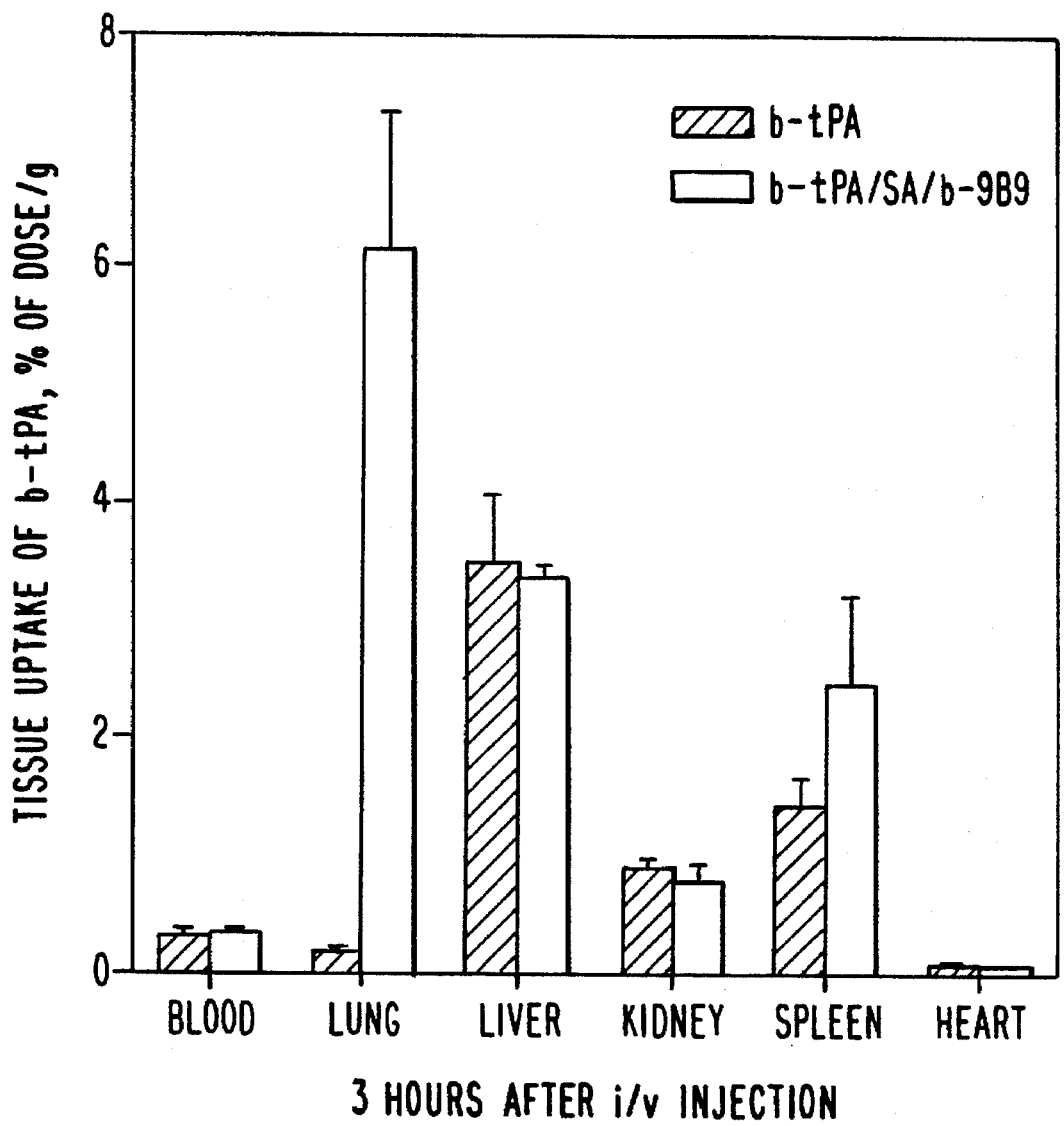
FIG. 7 is a bargraph showing the biodistribution in rats of radiolabeled tPA (hatched bars) and radiolabeled tPA conjugated with Mab 9B9 (unfilled bars) three hours after intravenous injection.
Figure 8:
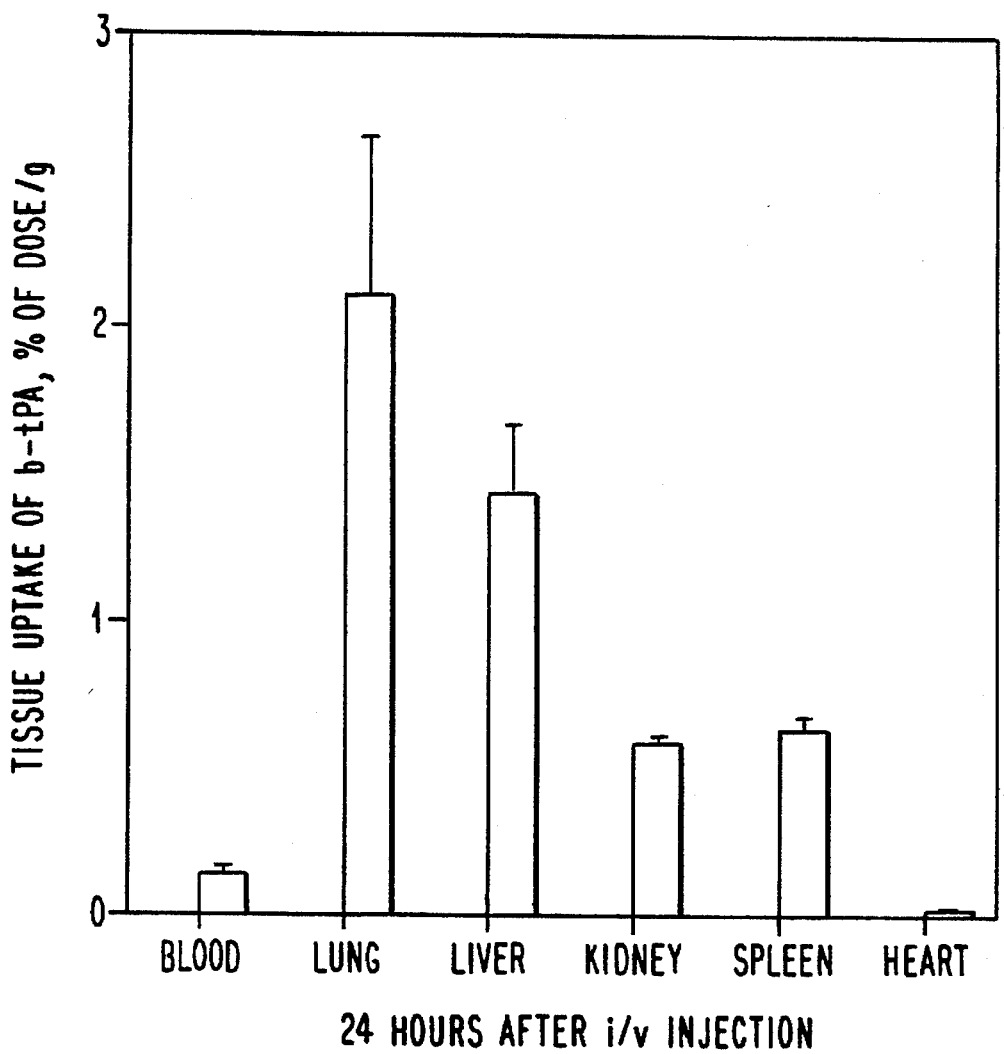
FIG. 8 is a bargraph showing the biodistribution in rats of radiolabeled tPA conjugated with Mab 9B9 twenty-four hours after intravenous injection.

In experiments with the plasminogen activators tPA, uPA and scuPA, conjugation with Mab 9B9 leads to a 10 to 20 fold increase in pulmonary accumulation of radiolabeled plasminogen activator as compared to conjugation of these activators with control isotype-matched IgG (FIGS. 1A, 1B and 1C). Blood levels of the Mab 9B9 conjugated plasminogen activator and the IgG conjugated plasminogen activator were the same (FIGS. 1A, 1B, and 1C). Accumulation of the plasminogen activators conjugated with Mab 9B9 in the lung was also greater than in the blood, liver, kidney, spleen and heart (FIGS. 2, 3 and 4). As shown in FIG. 5, pulmonary uptake of Mab 9B9-conjugated tPA occurs as soon as five minutes after intravenous injection in rats and is retained in the lung tissue for up to one day after the injection (FIGS. 6, 7 and 8).

Figure 9:
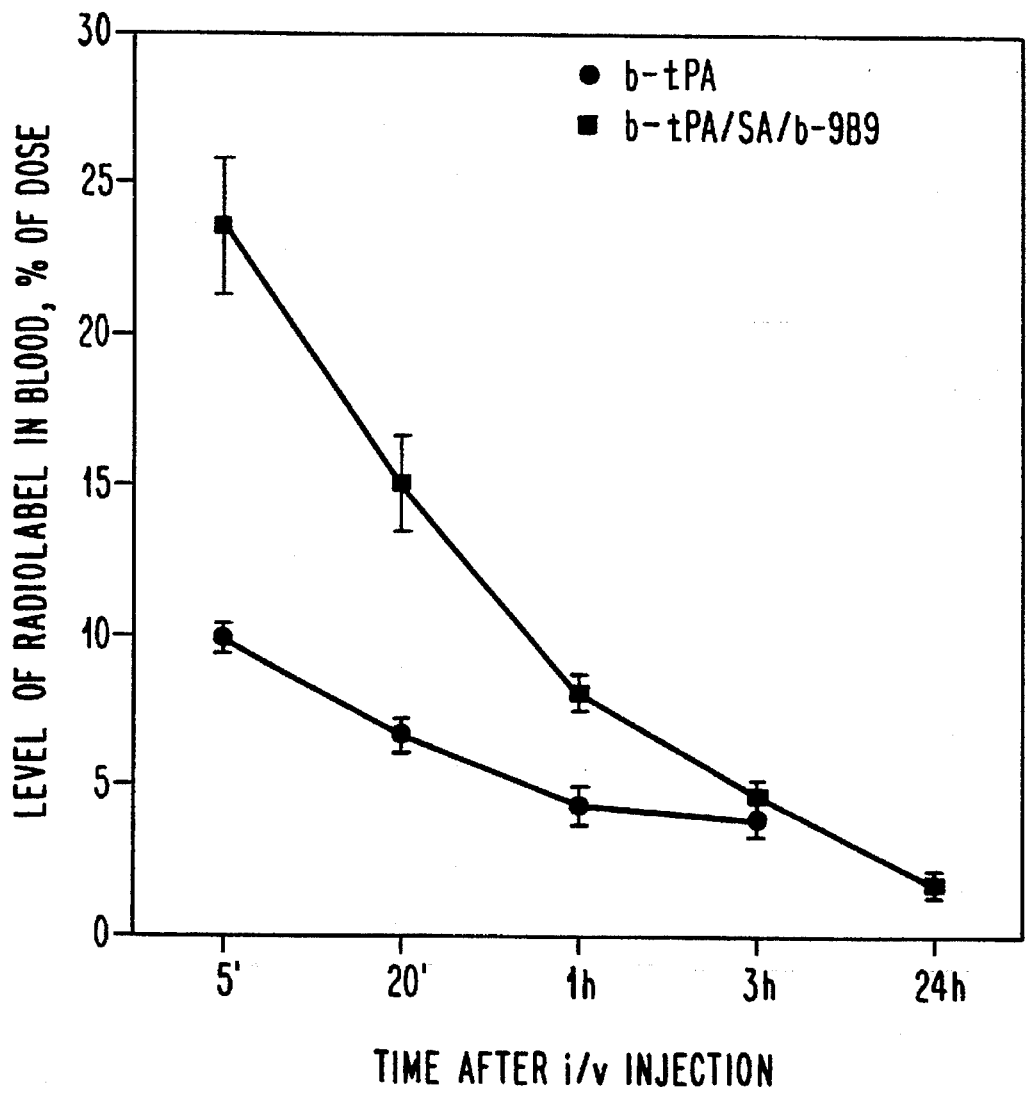
FIG. 9 is a linegraph showing the clearance in rats of radiolabeled tPA (filled circles) and radiolabeled tPA conjugated with Mab 9B9 (filled squares) as a measure of radiolabel in the blood versus time following intravenous injection.

It has also been found that Mab 9B9 conjugated plasminogen activators circulate in the bloodstream significantly longer than the plasminogen activators alone. In experiments with Mab 9B9-conjugated tPA, it was shown that the Mab 9B9-conjugated tPA remained in the blood at higher concentrations and for a significantly longer period of time than tPA alone (FIG. 9).

The production of hybridoma cells capable of producing monoclonal antibodies to ACE was first described in USSR Disclosure Number 3996711, registered on Feb. 8, 1987. Production of this antibody was also described by Danilov et al. in *Biotechnology and Applied Biochemistry* (1987) 9:319–322. Purification methods for increasing specificity and efficacy of this antibody in its targeting into the lung were taught by Hiemisch et al. *Nucl. Med. Biol.* (1993) 20(4):435–441. This monoclonal antibody has been used in a number of different studies to determine localization of ACE in human tissues (Danilov et al. *Histochemistry* (1987) 87:487–490), for gamma scintigraphy visualization of the pulmonary vascular bed and detection of lung injury (Danilov et al. in *J. Mol. Cell Cardiol.* (1989) 21:165–170). The antibody was also radiolabeled for analysis of the kinetic distribution, lung accumulation and blood clearance and to determine the potential of the antibody as a diagnostic tool for lung vessel visualization (Danilov et al., *J. Nucl. Med.* (1989) 30:1686–1692). Accumulation of this antibody in the normal lung was demonstrated by Danilov et al. in *Laboratory Investigation* (1991) 64(1):118–124. Muzykantov, V. R. and Danilov S. M. *Int J. Radiat. Biol.* (1991) 60(1/2):11–15, conjugated glucose oxidase to this antibody and showed specific accumulation in the lung upon systemic administration. It was suggested that this complex could be used in investigations of vasculature as a target for selective cytotoxic action both in vitro and in vivo. Use of this antibody as a vector for targeted drug delivery to the lung has also been suggested by Danilov et al. in *J. Mol. Cell Cardiol.* (1989) 21:165–170 and Danilov, S. M. and Muzykantov, V. R. in *Progress in Respiration Research* (1990) 26:85–96. However, use of this antibody to deliver plasminogen activators to the pulmonary endothelium for the treatment of fibrin clots has not been suggested. In addition, the ability of this conjugated multimolecular complex to remain in the circulation at higher concentrations for longer periods of time than unconjugated plasminogen activators was unexpected based on the properties of Mab 9B9.

The plasminogen activators can be conjugated to Mab 9B9 to form the multimolecular complexes of the present invention by a number of different methods well known to those of skill in the art. For example, conjugation of Mab 9B9 with a plasminogen activator may be performed using a homo-bifunctional cross-linking agent. Such cross-linking agents offer conjugation of two proteins via chemical modification of the same functional groups on both proteins. Since all proteins contain amino groups, this class of cross-linkers usually produces intermolecular complexes by cross-linking of their amino groups. In one embodiment, the cross-linking agent disuccinimidylsubarate was incubated with proteins at equimolar ratios to cross-link the two proteins. Sakharov et al. *Thrombosis Res.* (1988) 49:481–488. Introduction of disulfide groups in two proteins by incubation with equimolar amounts of N-succinimidyl-3-(2-pyridildithio)propionate (SPDP) followed by reduction of the disulfide groups on one of the proteins also allows for conjugation of the two proteins. Cavallaro et al. *J. Biol. Chem.* (1993) 268:23186–23190. The hetero-bifunctional cross-linking agent, m-maleimidobenzoic acid N-hydroxysuccinimide ester can also be used for conjugating an SPDP-treated plasminogen activator with any protein including Mab 9B9 or, vice versa, SPDP-treated Mab 9B9 with a plasminogen activator. Plasminogen activators can also be coupled with the antibody using a bi-functional antibody chimera possessing affinity for both the plasminogen activator and the mouse IgG. In a preferred embodiment, streptavidin-biotin cross-linking is used. In this embodiment, both the antibody and plasminogen activator are modified with biotin ester which allows for further intermolecular conjugation of the biotinylated molecules by streptavidin. Streptavidin-mediated cross-linking of biotinylated proteins is a widely used biochemical method. The enzymatic activity of tPA and streptokinase is not reduced in the course of biotinylation, conjugation with streptavidin and with biotinylated Mab 9B9. In addition, the ability of the antibody to specifically target the lung is not altered by this process. Accordingly, streptavidin-mediated cross-linking of biotinylated plasminogen and biotinylated anti-ACE Mab 9B9 provides a new class of active fibrinolytic agents that accumulate in the lung and are retained in the lung for a prolonged period.

The multimolecular complexes of the present invention are administered systemically in an effective amount to an animal to selectively deliver plasminogen activators to the pulmonary endothelium. By "systemic administration" it is meant to include, but is not limited to, intravenous, intraarterial, intraperitoneal, intramuscular and intracutaneous administration. In addition, these complexes can be administered locally by intravascular administration via a vascular catheter, e.g., intracoronary or intrapulmonary administration. By "effective amount" it is meant a concentration of the multimolecular complex of the present invention which provides a sufficient concentration of the plasminogen activator to the pulmonary endothelium to activate plasmin in that area. Such concentrations can be routinely determined by those of skill in the art based upon the present disclosure and what is known in the art about the specific plasminogen activator being used. In a preferred embodiment, these concentrations may range from about 1 to about 100 mg/70 kg. However, other appropriate concentrations may be determined by examining the local fibrinolytic effect of a complex of the present invention.

The local fibrinolytic effect of these complexes may be estimated in animals by injection of the complex after injection of radiolabeled fibrin microthrombi, which accumulate in the pulmonary microvasculature due to mechanical capture. This procedure may be performed in vivo, by systemic i.v. injection or in an isolated perfused lung model. Release of radioactivity from the lung into the circulation or perfusate will characterize rate and effectiveness of the fibrinolysis in the pulmonary vasculature. In humans, effectiveness of pulmonary or cardiac fibrinolysis can be assessed by evaluation of restoration of the blood flow in an occluded vessel or vasculature area. For this purpose, pulmonary blood circulation may be tested by comparison of the accumulation in the chest of systemically injected radiolabeled microspheres with intratracheally administered radiolabeled aerosols. Both tests are performed using a gamma camera and may be accompanied by standard X-ray examination of the chest. Detection of the generation of specific fibrin fragments by immunoassay using specific monoclonal antibodies to such fragments may also be used for monitoring fibrinolysis.

The multimolecular complexes of the present invention are administered in a pharmaceutically acceptable vehicle. Suitable pharmaceutically acceptable vehicles are well known in the art and are described, for example, in Gennaro, Alfonso, Ed., *Remington's Pharmaceutical Sciences*, 18th Edition, Mack Publishing Co., Easton, Pa., 1990, a standard reference text in this field. Pharmaceutical carriers may be selected in accordance with the intended route of administration and the standard pharmaceutical practice. For example, formulations for intravenous administration may include sterile aqueous solutions which may also contain buffers or other diluents. Appropriate pharmaceutical vehicles can be routinely determined by those of skill in the art. By "animal" it is meant to include, but is not limited to, mammals, fish, amphibians, reptiles, birds, marsupials, and most preferably, humans. The ability of Mab 9B9 to cross-react with ACE in a number of different animals including human, monkey, rat, cat and hamster ACE was demonstrated by Danilov et al. in *International Immunology* (1994) 6(8):1153–1160.

The multimolecular complex of the present invention can be administered to an animal to selectively and effectively deliver the enzymatically active plasminogen activator to the pulmonary endothelium to enhance fibrinolysis in the lungs and in the heart. By "enhancing" fibrinolysis it is meant to increase plasmin levels in the lung and heart, the first organ downstream form the lung, to concentrations such that fibrin is digested. Such enhancement can be determined routinely by those of skill in the art by measuring changes in prothrombin time, activated partial thromboplastin time or thrombin time. This method of delivery of the present invention overcomes problems associated with rapid clearance of the plasminogen activator observed in clinical trials as the multimolecular complex of the present invention has been shown to increase the circulation time of the plasminogen activator. It is believed that this method of delivery will also prevent rapid reocclusion which occurs. In addition, the selective delivery may alleviate bleeding which has been associated with administration of plasminogen activators.

The tissue selective accumulation of plasminogen activators in the lung also provides for effective fibrinolysis of secondary clots coming into the pulmonary circulation as a thromboemboli. Patients with deep venous thrombosis, having a high probability of such thromboembolism of the pulmonary vessels, are considered a preferred group for treatment with the multimolecular complexes of the present invention. Treatment with the multimolecular complexes of the present invention can prevent and treat the occlusion of pulmonary vessels by these thromboemboli.

The following nonlimiting examples are provided to further illustrate the present invention.

EXAMPLES

Example 1

Biotinylation of Mab 9B9 and plasminogen activators

Biotin ester, 6-biotinylaminocaproic acid N-hydroxysuccinimide ester was dissolved in 100% dimethyl formamide to a final concentration of 10 mM or 1 mM.

Eight μl of 1 mM biotin ester were added to 100 μl of Mab 9B9 or control IgG (1 mg/ml in borate buffered saline), while 2.5 μl of 10 mM biotin ester were added to 100 μl of plasminogen activator (1 mg/ml in borate buffered saline), so that the molar ratio of biotin ester/protein in all samples was 10. Following a 1 hour incubation on ice, excess biotin ester was removed by gel-filtration on G25-Sephadex following standard procedures.

Trimolecular complexes, biotinylated Mab 9B9/streptavidin/biotinylated plasminogen activator, were prepared by sequential incubation of biotinylated proteins with streptavidin. Specifically, 2 μl of biotinylated plasminogen activator (0.4 mg.ml) was mixed with 25 μl of phosphate buffered saline (PBS) containing 2 mg/ml BSA (PBS-BSA) and 5 μl streptavidin (1 mg/ml). This mixture was then incubated on ice for 1 hour. The mixture was divided into two equal portions of 15 μl each. To the first portion was added 10 μl of PBS-BSA containing 10 μg of biotinylated Mab 9B9. To the second portion was added 10 μl of biotinylated IgG (control). These mixtures were then incubated on ice for 2 hours.

Example 2

Determining blood levels, pulmonary uptake and biodistribution of radiolabeled plasminogen activators conjugated with Mab 9B9 or IgG To estimate biodistribution, blood clearance and pulmonary uptake of plasminogen activator, the plasminogen activators were radiolabeled with $^{125}$I by the conventional Iodogen technique as described by Hiemisch et al. *Nucl. Med. Biol.* (1993) 20:435–444. Trimolecular complexes, biotinylated Mab 9B9/streptavidin/$^{125}$I-biotinylated plasminogen activator, were prepared as described in Example 1. Rats were injected in the tail vein with 0.5 ml PBS-BSA containing 200 ng of a trimolecular complex. Control animals were injected with a trimolecular complex containing biotinylated IgG. Radioactivity in blood and tissues was determined as described by Muzykantov et al. *J. Nucl. Med.* (1994) 35:1358–1365. At predetermined time intervals, animals were sacrificed upon narcosis by desanguination. Blood was collected in 2 ml samples. Organs were removed from the body, washed with saline and weighed. Radioactivity in the blood and tissues was determined using an LKB-gamma counter.

What is claimed is:

1. A multimolecular complex comprising a plasminogen activator conjugated to anti-ACE Mab 9B9 which is capable of delivering the plasminogen activator to the pulmonary endothelium.

2. A method of selectively targeting a plasminogen activator to the pulmonary endothelium of an animal comprising conjugating the plasminogen activator to anti-ACE Mab 9B9 to form a multimolecular complex and administering an effective amount of said multimolecular complex to the animal.

* * * * *

UNITED STATES PATENT AND TRADEMARK OFFICE
CERTIFICATE OF CORRECTION

PATENT NO. : 5,653,979

DATED : August 5, 1997

INVENTOR(S) : Muzykantov et al.

It is certified that error appears in the above-indentified patent and that said Letters Patent is hereby corrected as shown below:

At col 1, line 57, please delete "783" insert therefor --793--.

At col 2, line 64, please delete "Fig. 1 is a bargraph" and insert therefor --Figures 1A-1C are bargraphs--.

Signed and Sealed this

Eighth Day of September, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,653,979  
APPLICATION NO. : 08/413415  
DATED : August 5, 1997  
INVENTOR(S) : Muzykantov et al.

Page 1 of 1

It is certified that error appears in the above-identified patent and that said Letters Patent is hereby corrected as shown below:

Title page, item [75] inventor: add -- Sergei M. Danilov --

Signed and Sealed this

Twenty-sixth Day of August, 2008

JON W. DUDAS  
*Director of the United States Patent and Trademark Office*